United States Patent
Allen et al.

(10) Patent No.: US 10,430,508 B2
(45) Date of Patent: *Oct. 1, 2019

(54) SYSTEM AND METHOD FOR ANALYZING AND DEDUCING CRITERIA-RELATED CONTENT FOR EVALUATION

(71) Applicant: International Business Machines Corporation, Armonk, NY (US)

(72) Inventors: Corville O. Allen, Morrisville, NC (US); Ovies C. Brabson, Raleigh, NC (US); Kathryn M. Whaley, Rochester, MN (US); Saeid Sakhitab, Rochester, MN (US); Eric Woods, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 224 days.

This patent is subject to a terminal disclaimer.

(21) Appl. No.: 14/861,023

(22) Filed: Sep. 22, 2015

(65) Prior Publication Data
US 2016/0147727 A1    May 26, 2016

Related U.S. Application Data

(63) Continuation of application No. 14/554,481, filed on Nov. 26, 2014.

(51) Int. Cl.
*G16H 10/40*    (2018.01)
*G06F 17/24*    (2006.01)

(52) U.S. Cl.
CPC ........... *G06F 17/241* (2013.01); *G16H 10/40* (2018.01)

(58) Field of Classification Search
CPC ...... G06F 17/241; G06F 17/24; G06F 17/243; G06F 17/248; G06F 19/30; G06F 19/366; G06F 19/32; G16H 10/40
See application file for complete search history.

(56) References Cited

U.S. PATENT DOCUMENTS 5,583,758 A * 12/1996 McIlroy ............... G06F 19/325
                                                          705/2
6,009,442 A * 12/1999 Chen ................. G06F 17/30696
                                                     707/E17.082

(Continued)

OTHER PUBLICATIONS

H. Cui et al., "Question answering passage retrieval using dependency relations," Proceedings of the 28th annual international ACM SIGIR conference on Research and development in information retrieval, ACM, 2005.

(Continued)

*Primary Examiner* — Thu V Huynh
(74) *Attorney, Agent, or Firm* — Terrile, Cannatti & Chambers, LLP; Stephen A. Terrile

(57) ABSTRACT

A method, system and computer-usable medium are disclosed for analyzing and deducing criteria-related content for evaluation in a system capable of answering questions. A criteria text is processed to identify criteria. The criteria text is then analyzed to identify a set of criteria-related content associated with the criteria, which in turn is processed to determine its relationship to the criteria. Once the relationship has been determined, the set of criteria-related content is annotated accordingly. The set of criteria-related content is then used in accordance with its annotation when processing the criteria for evaluation.

5 Claims, 8 Drawing Sheets

(56) References Cited

U.S. PATENT DOCUMENTS

| | | | |
|---|---|---|---|
| 8,000,956 B2 | 8/2011 | Brun et al. | |
| 9,336,269 B1* | 5/2016 | Smith | G06F 17/30424 |
| 2005/0256866 A1* | 11/2005 | Lu | G06F 17/30867 |
| 2007/0078814 A1 | 4/2007 | Flowers et al. | |
| 2009/0070103 A1* | 3/2009 | Beggelman | G06F 17/27 |
| | | | 704/9 |
| 2012/0078837 A1* | 3/2012 | Bagchi | A61B 5/00 |
| | | | 706/52 |
| 2013/0246098 A1* | 9/2013 | Habboush | G06Q 10/10 |
| | | | 705/3 |
| 2013/0304742 A1 | 11/2013 | Roman et al. | |
| 2014/0058742 A1* | 2/2014 | Chari | G06F 19/345 |
| | | | 705/2 |
| 2014/0258205 A1* | 9/2014 | Clark | G06N 5/02 |
| | | | 706/46 |
| 2014/0297571 A1 | 10/2014 | Beamon et al. | |
| 2015/0356089 A1* | 12/2015 | Jamrog | G06F 17/3053 |
| | | | 707/723 |
| 2016/0110520 A1* | 4/2016 | Dettman | G06F 19/3475 |
| | | | 705/2 |
| 2017/0132141 A1* | 5/2017 | Allen | G06F 12/0888 |
| 2017/0316063 A1* | 11/2017 | Clifford | G06F 17/3087 |

OTHER PUBLICATIONS

R. High, "The Era of Cognitive Systems: An Inside Look at IBM Watson and How it Works," IBM Redbooks, 2012.

Yuan et al., "Watson and Healthcare," IBM developerWorks, 2011.

IBM, Journal of Research and Development, This is Watson, Introduction and Table of Contents, vol. 56, No. 3/4, May/Jul. 2012, http://ieeexplore.ieee.org/xpl/tocresult.jsp?reload=true&isnumber=6177717.

List of IBM Patents or Applications Treated as Related.

* cited by examiner

Evidence

| Supporting Evidence | Response & Adverse Events | Eligibility | Contraindications |

View: ● All ○ Action Required ○ Completed ○ Open All

⌐ 404 Criteria Text

Inclusion

- ▶ 1  Signed IRB-approved informed consent document
- ▶ 2  Age 18 to 60; Patient above the age of 60 only with PI approval
  - ■ PI Approval
  - ☑ Age 18 to 60                    29
  - △ Above the age of 60              29
- ▼ 3  Diagnosis of newly diagnosed AML (other than acute promyelocytic leukemia (APL)) or ch-risk (intermediate-2 or high by IPSS or 10% blasts (including CMML) MDS. Prior therapy with hydrea and the use of a single or a two day dose of cytarabine (up to 3 g/m2) for emergency use of up to 24 hours prior to start of study therapy is allowed. Prior therapy for MDS and other AHD is not allowed.
  - ■ Emergency Use
  - ☑ AML                              AML
  - △ APL                              AML
  - △ GMML                             AML
  - △ MDS                              AML
  - △ MDS                              AML
  - ■ AHD
  - △ Newly Diagnosed                  False
  - ■ Intermediate - 2

Exclusion

- ▶ 4  ECOG performance status of <=3 at study entry.
- ▶ 5  Organ function as defined below (unless due to leukemia). Serum creatinine <=3 mg/dL, Total bilirubin <=2.5 mg/dL, AL (SGPT) <=3 ULN or <=5 x ULN if related to disease.
- ▶ 6  Women of child-bearing potential must have a negative serum or urine pregnancy test within 7 days and must agree to practice acceptable contraceptive methods. Men must agree not to father a child and agree to use a condom if his partner is of child bearing potential.
- ▶ 7  Cardiac ejection fraction >= 40% (by either cardiac echo or MUGA scan). Documentation of recent (<=6 months from screening) outside reports is acceptable.
- ▶ 8  Breast feeding females
- ▶ 9  Patients with active infections (viral, bacterial, and fungal are not eligible.
- ▶ 10 Patients with active secondary malignancy will not be eligible.

402

⌐ 406  Criteria-Related Content Visualized in Error

FIGURE 4

SYSTEM AND METHOD FOR ANALYZING AND DEDUCING CRITERIA-RELATED CONTENT FOR EVALUATION

This is a continuation of U.S. patent application Ser. No. 14/554,481, filed Nov. 26, 2014, entitled "System and Method for Analyzing and Deducing Criteria-Related Content for Evaluation," which is incorporated herein by reference in its entirety.

BACKGROUND OF THE INVENTION

Field of the Invention

The present invention relates in general to the field of computers and similar technologies, and in particular to software utilized in this field. Still more particularly, it relates to a method, system and computer-usable medium for analyzing and deducing criteria-related content for evaluation.

Description of the Related Art

When patients are seen, treated, or tested by medical practitioners and clinicians, the events of the interaction are recorded and become part of the patient's medical records. Maintenance of such medical records is an important element of modern medical treatment. Recently, the technology used for recording and archiving medical records has been undergoing an evolution. Modern medical and health care institutions are now adopting electronic medical records systems instead of traditional paper recording systems. Such computerized record keeping systems offer significant advantages to the practitioners, the patient, and the healthcare system as a whole.

Many medical and healthcare institutions also maintain a set of treatment guidelines for clinical trials or other guideline-based systems. These guidelines typically include established criteria, which are usually the product of long-term clinical studies, the results of which are peer reviewed and published in established medical journals. Such criteria are often written with clarifications, restrictions and definitions, which may augment the criteria or can be ignored. As an example, a clinical trial may be conducted that includes women of childbearing potential and men who do not practice contraception, with non-childbearing is defined as =>1 year postmenopausal or surgically sterilized. In this example, the definition of non-childbearing is a criteria clarification that can be excluded during criteria processing.

Conversely, certain criteria may contain clarifications or definitions that should be treated as an augmentation to the criteria during processing. For example, a criteria for a clinical trial may state that uncontrolled hypothermia (blast>=20, no hemoglobin medicine) should not be eligible for this treatment. While hypothermia is typically defined as a blast>15, the clarification within the criteria states that blast>=20 is the definition for uncontrolled hypothermia in the trial. As a result, the clarification is an augmentation to the criteria, which should be included when the criteria is processed. However, current systems lack the ability to deduce when these clarifications, restrictions and definitions should either be ignored or treated as an augmentation when the criteria is processed. Furthermore, this inability may skew how a given criteria is evaluated by a machine.

SUMMARY OF THE INVENTION

A method, system and computer-usable medium are disclosed for analyzing and deducing criteria-related content for evaluation in a system capable of answering questions. In various embodiments, a criteria text is processed to identify criteria. The criteria text is then analyzed to identify a set of criteria-related content associated with the criteria, which in turn is processed to determine its relationship to the criteria. Once the relationship has been determined, the set of criteria-related content is annotated accordingly. The set of criteria-related content is then used in accordance with its annotation when processing the criteria for evaluation.

In various embodiments, the set of criteria-related content is identified by a trigger associated with the criteria. In these embodiments, the trigger may be a set of parentheses, a set of brackets, a colon, a line indent, or a definition. In certain embodiments, the relationship of the set of criteria-related content to the criteria may be a statement, a definition, a clarification, a restriction, a formula, a range of values, or a list. In various embodiments, the annotation of the set of criteria-related content may be "augmentation content" or "ignored content." In certain embodiments, the criteria is associated with elements of a medical trial.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

FIG. 4 shows the display of criteria and criteria-related content that has been visualized in error within a user interface.

DETAILED DESCRIPTION

Figure 1:
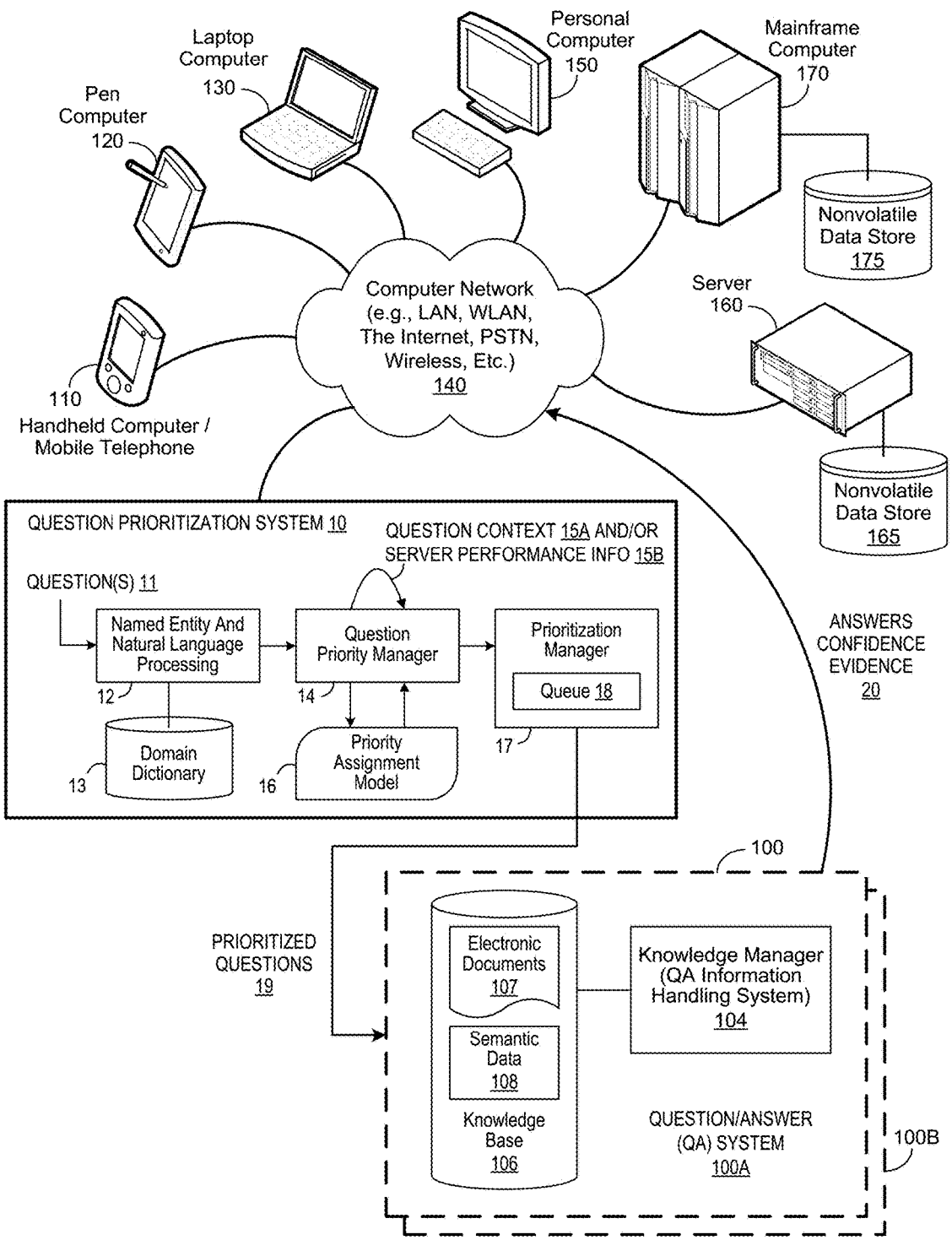
FIG. 1 depicts an exemplary client computer in which the present invention may be implemented.

A method, system and computer-usable medium are disclosed for analyzing and deducing criteria-related content for evaluation in a system capable of answering questions. The present invention may be a system, a method, and/or a computer program product. In addition, selected aspects of the present invention may take the form of an entirely hardware embodiment, an entirely software embodiment (including firmware, resident software, micro-code, etc.) or an embodiment combining software and/or hardware aspects that may all generally be referred to herein as a "circuit," "module" or "system." Furthermore, aspects of the present invention may take the form of computer program product embodied in a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a dynamic or static random access memory (RAM), a read-only memory (ROM), an erasable programmable read-only memory (EPROM or Flash memory), a magnetic storage device, a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server or cluster of servers. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

FIG. 1 depicts a schematic diagram of one illustrative embodiment of a question prioritization system 10 and question/answer (QA) system 100 connected to a computer network 140. The QA system 100 includes a knowledge manager 104 that is connected to a knowledge base 106 and configured to provide question/answer (QA) generation functionality for one or more content users who submit across the network 140 to the QA system 100. To assist with efficient sorting and presentation of questions to the QA system 100, the prioritization system 10 may be connected to the computer network 140 to receive user questions, and may include a plurality of subsystems which interact with cognitive systems, like the knowledge manager 100, to prioritize questions or requests being submitted to the knowledge manager 100.

The Named Entity subsystem 12 receives and processes each question 11 by using natural language (NL) processing to analyze each question and extract question topic information contained in the question, such as named entities, phrases, urgent terms, and/or other specified terms which are stored in one or more domain entity dictionaries 13. By leveraging a plurality of pluggable domain dictionaries relating to different domains or areas (e.g., travel, healthcare, electronics, game shows, financial services), the domain dictionary 11 enables critical and urgent words (e.g., "threat level") from different domains (e.g., "travel") to be identified in each question based on their presence in the domain dictionary 11. To this end, the Named Entity subsystem 12 may use a Natural Language Processing (NLP) routine to identify the question topic information in each question. As used herein, "NLP" refers to the field of computer science, artificial intelligence, and linguistics concerned with the interactions between computers and human (natural) languages. In this context, NLP is related to the area of human-computer interaction and natural language understanding by computer systems that enable computer systems to derive meaning from human or natural language input. For example, NLP can be used to derive meaning from a human-oriented question such as, "What is tallest mountain in North America?" and to identify specified terms, such as named entities, phrases, or urgent terms contained in the question. The process identifies key terms and attributes in the question and compares the identified terms to the stored terms in the domain dictionary 13.

The Question Priority Manager subsystem 14 performs additional processing on each question to extract question context information 15A. In addition or in the alternative, the Question Priority Manager subsystem 14 may also extract server performance information 15B for the question prioritization system 10 and/or QA system 100. In selected embodiments, the extracted question context information 15A may include data that identifies the user context and location when the question was submitted or received. For example, the extracted question context information 15A may include data that identifies the user who submitted the question (e.g., through login credentials), the device or computer which sent the question, the channel over which the question was submitted, the location of the user or device that sent the question, any special interest location indicator (e.g., hospital, public-safety answering point, etc.), or other context-related data for the question. The Question Priority Manager subsystem 14 may also determine or extract selected server performance data 15B for the processing of each question. In selected embodiments, the server performance information 15B may include operational metric data relating to the available processing resources at the question prioritization system 10 and/or QA system 100, such as operational or run-time data, CPU utilization data, available disk space data, bandwidth utilization data, etc. As part of the extracted information 15A/B, the Question Priority Manager subsystem 14 may identify the SLA or QoS processing requirements that apply to the question being analyzed, the history of analysis and feedback for the question or submitting user, and the like. Using the question topic information and extracted question context and/or server performance information, the Question Priority Manager subsystem 14 is configured to populate feature values for the Priority Assignment Model 16 which provides a machine learning predictive model for generating a target priority values for the question, such as by using an artificial intelligence (AI) rule-based logic to determine and assign a question urgency value to each question for purposes of prioritizing the response processing of each question by the QA system 100.

The Prioritization Manager subsystem 17 performs additional sort or rank processing to organize the received questions based on at least the associated target priority values such that high priority questions are put to the front of a prioritized question queue 18 for output as prioritized questions 19. In the question queue 18 of the Prioritization Manager subsystem 17, the highest priority question is placed at the front for delivery to the assigned QA system 100. In selected embodiments, the prioritized questions 19 from the Prioritization Manager subsystem 17 that have a specified target priority value may be assigned to a specific pipeline (e.g., QA System 100A) in the QA system cluster 100. As will be appreciated, the Prioritization Manager subsystem 17 may use the question queue 18 as a message queue to provide an asynchronous communications protocol for delivering prioritized questions 19 to the QA system 100 such that the Prioritization Manager subsystem 17 and QA system 100 do not need to interact with a question queue 18 at the same time by storing prioritized questions in the question queue 18 until the QA system 100 retrieves them. In this way, a wider asynchronous network supports the passing of prioritized questions as messages between different computer systems 100A, 100B, connecting multiple applications and multiple operating systems. Messages can also be passed from queue to queue in order for a message to reach the ultimate desired recipient. An example of a commercial implementation of such messaging software is IBM's WebSphere MQ (previously MQ Series). In selected embodiments, the organizational function of the Prioritization Manager subsystem 17 may be configured to convert over-subscribing questions into asynchronous responses, even if they were asked in a synchronized fashion.

The QA system 100 may include one or more QA system pipelines 100A, 100B, each of which includes a computing device 104 (comprising one or more processors and one or more memories, and potentially any other computing device elements generally known in the art including buses, storage devices, communication interfaces, and the like) for processing questions received over the network 140 from one or more users at computing devices (e.g., 110, 120, 130) connected over the network 140 for communication with each other and with other devices or components via one or more wired and/or wireless data communication links, where each communication link may comprise one or more of wires, routers, switches, transmitters, receivers, or the like. In this networked arrangement, the QA system 100 and network 140 may enable question/answer (QA) generation functionality for one or more content users. Other embodiments of QA system 100 may be used with components, systems, sub-systems, and/or devices other than those that are depicted herein.

In each QA system pipeline 100A, 100B, a prioritized question 19 is received and prioritized for processing to generate an answer 20. In sequence, prioritized questions 19 are dequeued from the shared question queue 18, from which they are dequeued by the pipeline instances for processing in priority order rather than insertion order. In selected embodiments, the question queue 18 may be implemented based on a "priority heap" data structure. During processing within a QA system pipeline (e.g., 100A), questions may be split into many subtasks which run concurrently. A single pipeline instance can process a number of questions concurrently, but only a certain number of subtasks. In addition, each QA system pipeline may include a prioritized queue (not shown) to manage the processing order of these subtasks, with the top-level priority corresponding to the time that the corresponding question started (earliest has highest priority). However, it will be appreciated that such internal prioritization within each QA system pipeline may be augmented by the external target priority values generated for each question by the Question Priority Manager subsystem 14 to take precedence or ranking priority over the question start time. In this way, more important or higher priority questions can "fast track" through the QA system pipeline if it is busy with already-running questions.

In the QA system 100, the knowledge manager 104 may be configured to receive inputs from various sources. For example, knowledge manager 104 may receive input from the question prioritization system 10, network 140, a knowledge base or corpus of electronic documents 106 or other data, a content creator 108, content users, and other possible sources of input. In selected embodiments, some or all of the inputs to knowledge manager 104 may be routed through the network 140 and/or the question prioritization system 10. The various computing devices (e.g., 110, 120, 130, 150, 160, 170) on the network 140 may include access points for content creators and content users. Some of the computing devices may include devices for a database storing the corpus of data as the body of information used by the knowledge manager 104 to generate answers to cases. The network 140 may include local network connections and remote connections in various embodiments, such that knowledge manager 104 may operate in environments of any size, including local and global, e.g., the Internet. Additionally, knowledge manager 104 serves as a front-end system that can make available a variety of knowledge extracted from or represented in documents, network-accessible sources and/or structured data sources. In this manner, some processes populate the knowledge manager with the knowledge manager also including input interfaces to receive knowledge requests and respond accordingly.

In one embodiment, the content creator creates content in a document 106 for use as part of a corpus of data with knowledge manager 104. The document 106 may include any file, text, article, or source of data (e.g., scholarly articles, dictionary definitions, encyclopedia references, and the like) for use in knowledge manager 104. Content users may access knowledge manager 104 via a network connection or an Internet connection to the network 140, and may input questions to knowledge manager 104 that may be answered by the content in the corpus of data. As further described below, when a process evaluates a given section of a document for semantic content, the process can use a variety of conventions to query it from the knowledge manager. One convention is to send a well-formed question. Semantic content is content based on the relation between signifiers, such as words, phrases, signs, and symbols, and what they stand for, their denotation, or connotation. In other words, semantic content is content that interprets an expression, such as by using Natural Language (NL) Processing. In one embodiment, the process sends well-formed questions (e.g., natural language questions, etc.) to the knowledge manager. Knowledge manager 104 may interpret the question and provide a response to the content user containing one or more answers to the question. In some embodiments, knowledge manager 104 may provide a response to users in a ranked list of answers.

In some illustrative embodiments, QA system 100 may be the IBM Watson™ QA system available from International Business Machines Corporation of Armonk, New York, which is augmented with the mechanisms of the illustrative embodiments described hereafter. The IBM Watson™ knowledge manager system may receive an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question.

The IBM Watson™ QA system then performs deep analysis on the language of the input prioritized question 19 and the language used in each of the portions of the corpus of data found during the application of the queries using a variety of reasoning algorithms. There may be hundreds or even thousands of reasoning algorithms applied, each of which performs different analysis, e.g., comparisons, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the IBM Watson™ QA system. The statistical model may then be used to summarize a level of confidence that the IBM Watson™ QA system has regarding the evidence that the potential response, i.e. candidate answer, is inferred by the question. This process may be repeated for each of the candidate answers until the IBM Watson™ QA system identifies candidate answers that surface as being significantly stronger than others and thus, generates a final answer, or ranked set of answers, for the input question. The QA system 100 then generates an output response or answer 20 with the final answer and associated confidence and supporting evidence. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

Types of information processing systems that can utilize QA system 100 range from small handheld devices, such as handheld computer/mobile telephone 110 to large mainframe systems, such as mainframe computer 170. Examples of handheld computer 110 include personal digital assistants (PDAs), personal entertainment devices, such as MP3 players, portable televisions, and compact disc players. Other examples of information processing systems include pen, or tablet, computer 120, laptop, or notebook, computer 130, personal computer system 150, and server 160. As shown, the various information processing systems can be networked together using computer network 140. Types of computer network 140 that can be used to interconnect the various information processing systems include Local Area Networks (LANs), Wireless Local Area Networks (WLANs), the Internet, the Public Switched Telephone Network (PSTN), other wireless networks, and any other network topology that can be used to interconnect the information processing systems. Many of the information processing systems include nonvolatile data stores, such as hard drives and/or nonvolatile memory. Some of the information processing systems may use separate nonvolatile data stores (e.g., server 160 utilizes nonvolatile data store 165, and mainframe computer 170 utilizes nonvolatile data store 175). The nonvolatile data store can be a component that is external to the various information processing systems or can be internal to one of the information processing systems. An illustrative example of an information processing system showing an exemplary processor and various components commonly accessed by the processor is shown in FIG. 2.

Figure 2:
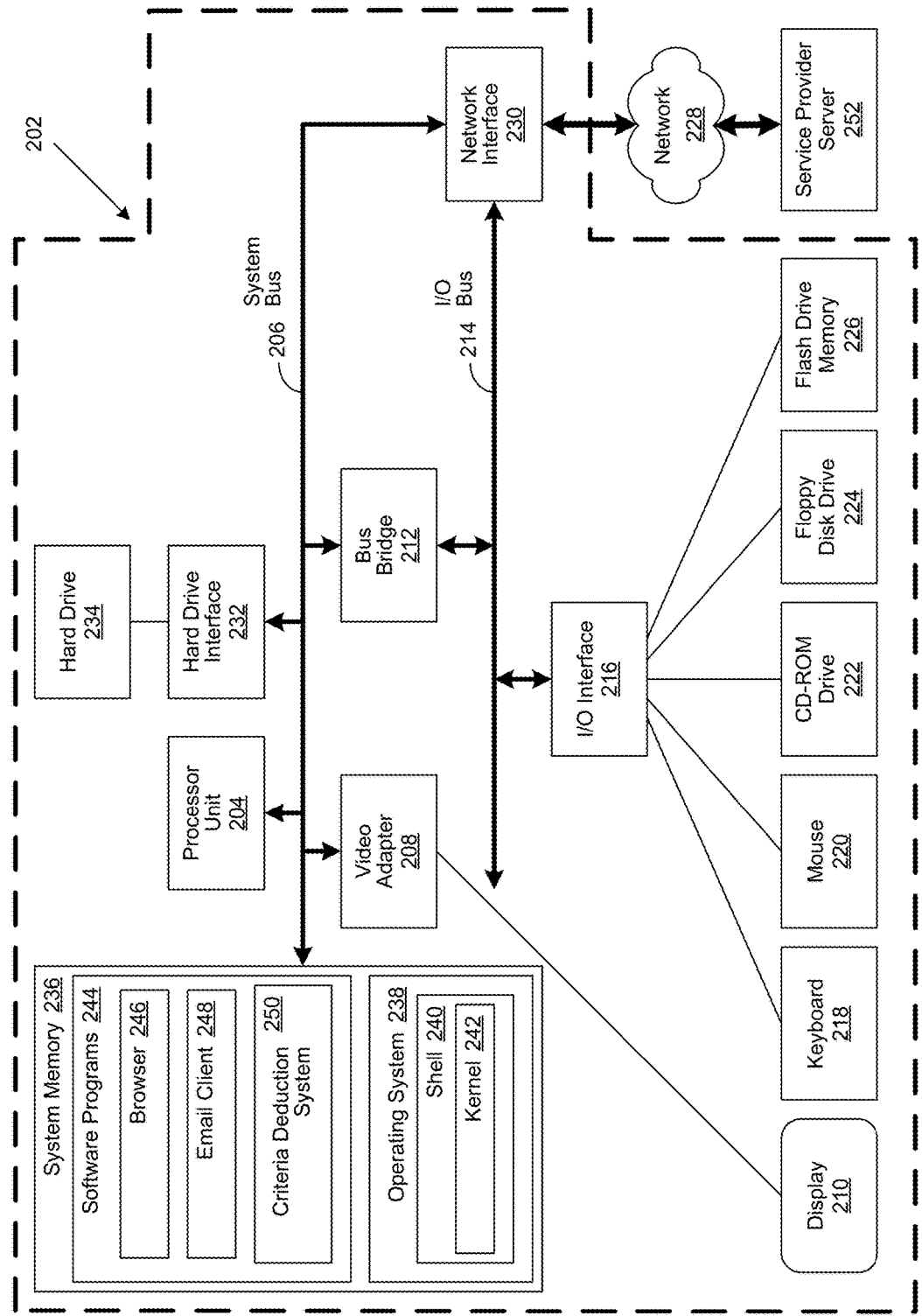
FIG. 2 is a simplified block diagram of an information handling system capable of performing computing operations.

FIG. 2 illustrates an information processing system 202, more particularly, a processor and common components, which is a simplified example of a computer system capable of performing the computing operations described herein. Information processing system 202 includes a processor unit 204 that is coupled to a system bus 206. A video adapter 208, which controls a display 210, is also coupled to system bus 206. System bus 206 is coupled via a bus bridge 212 to an Input/Output (I/O) bus 214. An I/O interface 216 is coupled to I/O bus 214. The I/O interface 216 affords communication with various I/O devices, including a keyboard 218, a mouse 220, a Compact Disk-Read Only Memory (CD-ROM) drive 222, a floppy disk drive 224, and a flash drive memory 226. The format of the ports connected to I/O interface 216 may be any known to those skilled in the art of computer architecture, including but not limited to Universal Serial Bus (USB) ports.

The information processing system 202 is able to communicate with a service provider server 252 via a network 228 using a network interface 230, which is coupled to system bus 206. Network 228 may be an external network such as the Internet, or an internal network such as an Ethernet Network or a Virtual Private Network (VPN). Using network 228, client computer 202 is able to use the present invention to access service provider server 252.

A hard drive interface 232 is also coupled to system bus 206. Hard drive interface 232 interfaces with a hard drive 234. In a preferred embodiment, hard drive 234 populates a system memory 236, which is also coupled to system bus 206. Data that populates system memory 236 includes the information processing system's 202 operating system (OS) 238 and software programs 244.

OS 238 includes a shell 240 for providing transparent user access to resources such as software programs 244. Generally, shell 240 is a program that provides an interpreter and an interface between the user and the operating system. More specifically, shell 240 executes commands that are entered into a command line user interface or from a file. Thus, shell 240 (as it is called in UNIX®), also called a command processor in Windows®, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 242) for processing. While shell 240 generally is a text-based, line-oriented user interface, the present invention can also support other user interface modes, such as graphical, voice, gestural, etc.

As depicted, OS 238 also includes kernel 242, which includes lower levels of functionality for OS 238, including essential services required by other parts of OS 238 and software programs 244, including memory management, process and task management, disk management, and mouse and keyboard management. Software programs 244 may include a browser 246 and email client 248. Browser 246 includes program modules and instructions enabling a World Wide Web (WWW) client (i.e., information processing system 202) to send and receive network messages to the Internet using HyperText Transfer Protocol (HTTP) messaging, thus enabling communication with service provider server 252. In various embodiments, software programs 244 may also include a criteria deduction system 250. In these and other embodiments, the criteria deduction system 250 includes code for implementing the processes described hereinbelow. In one embodiment, information processing system 202 is able to download the criteria deduction system 250 from a service provider server 252.

The hardware elements depicted in the information processing system 202 are not intended to be exhaustive, but rather are representative to highlight components used by the present invention. For instance, the information processing system 202 may include alternate memory storage devices such as magnetic cassettes, Digital Versatile Disks (DVDs), Bernoulli cartridges, and the like. These and other variations are intended to be within the spirit, scope and intent of the present invention.

Figure 3:
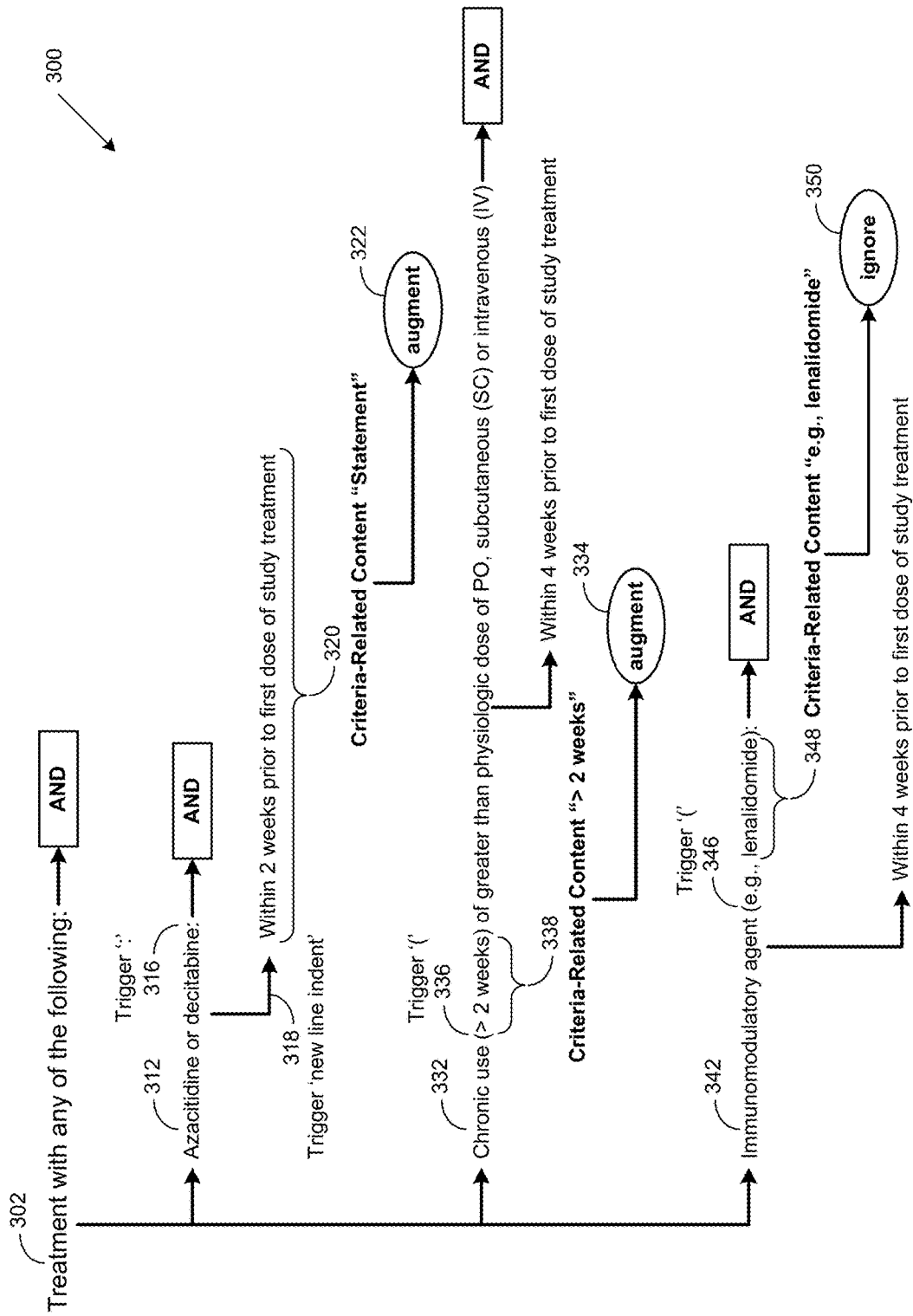
FIG. 3 is a generalized depiction of criteria-related content deductions.
Figure 5A:
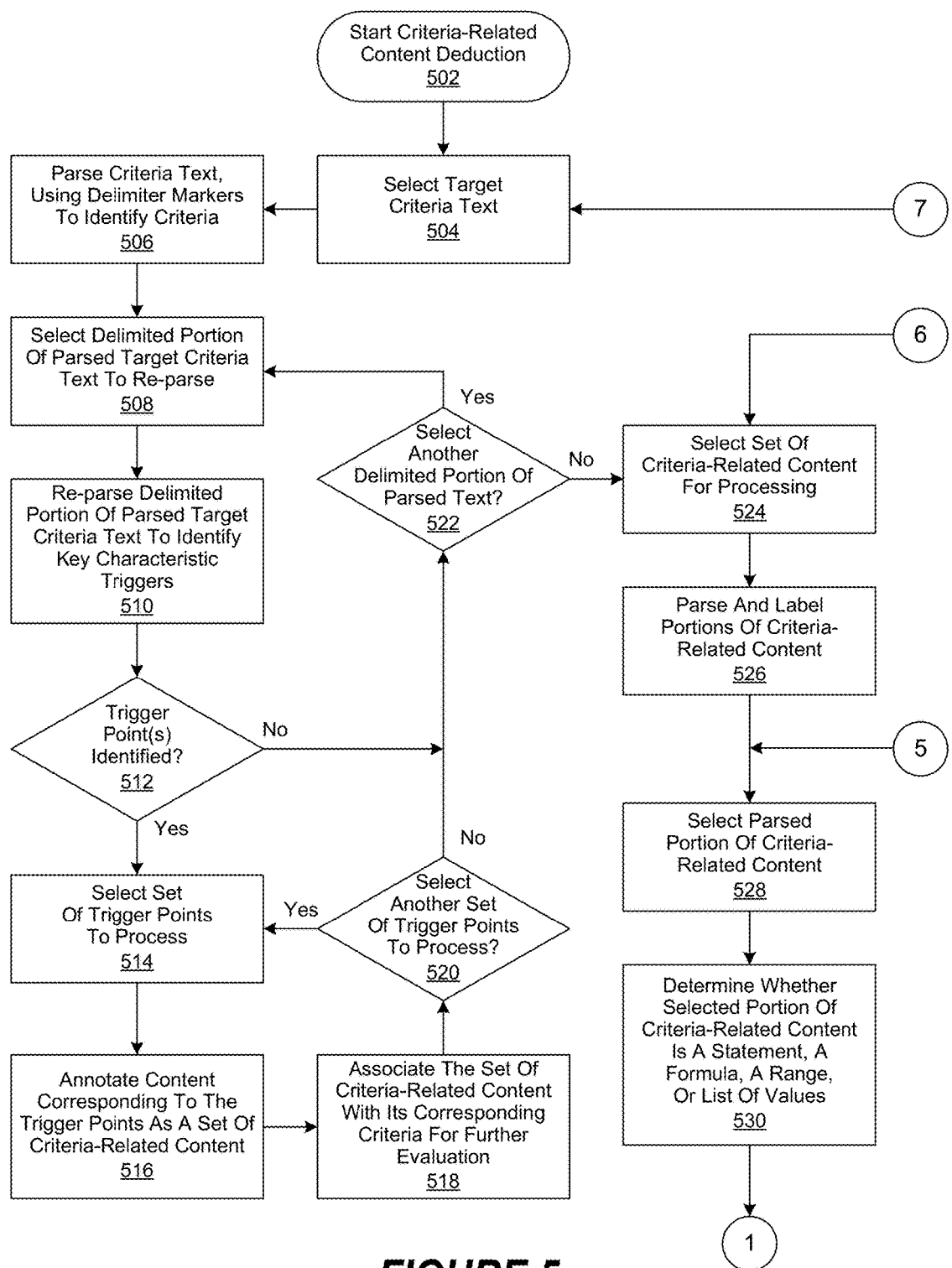
FIGS. 5A through 5D are a generalized flowchart of the performance of criteria-related content deduction operations.
Figure 5B:
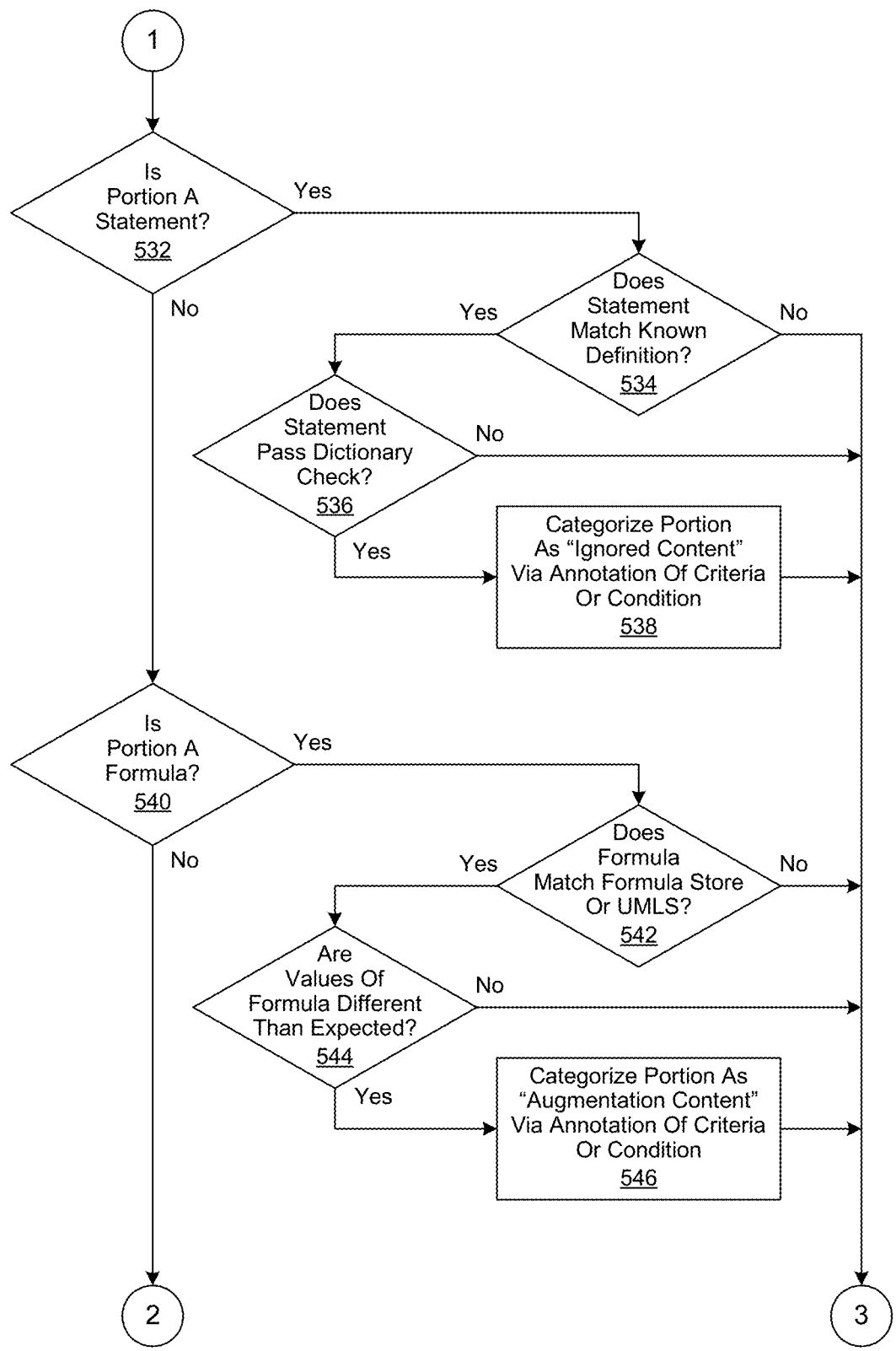
Figure 5C:
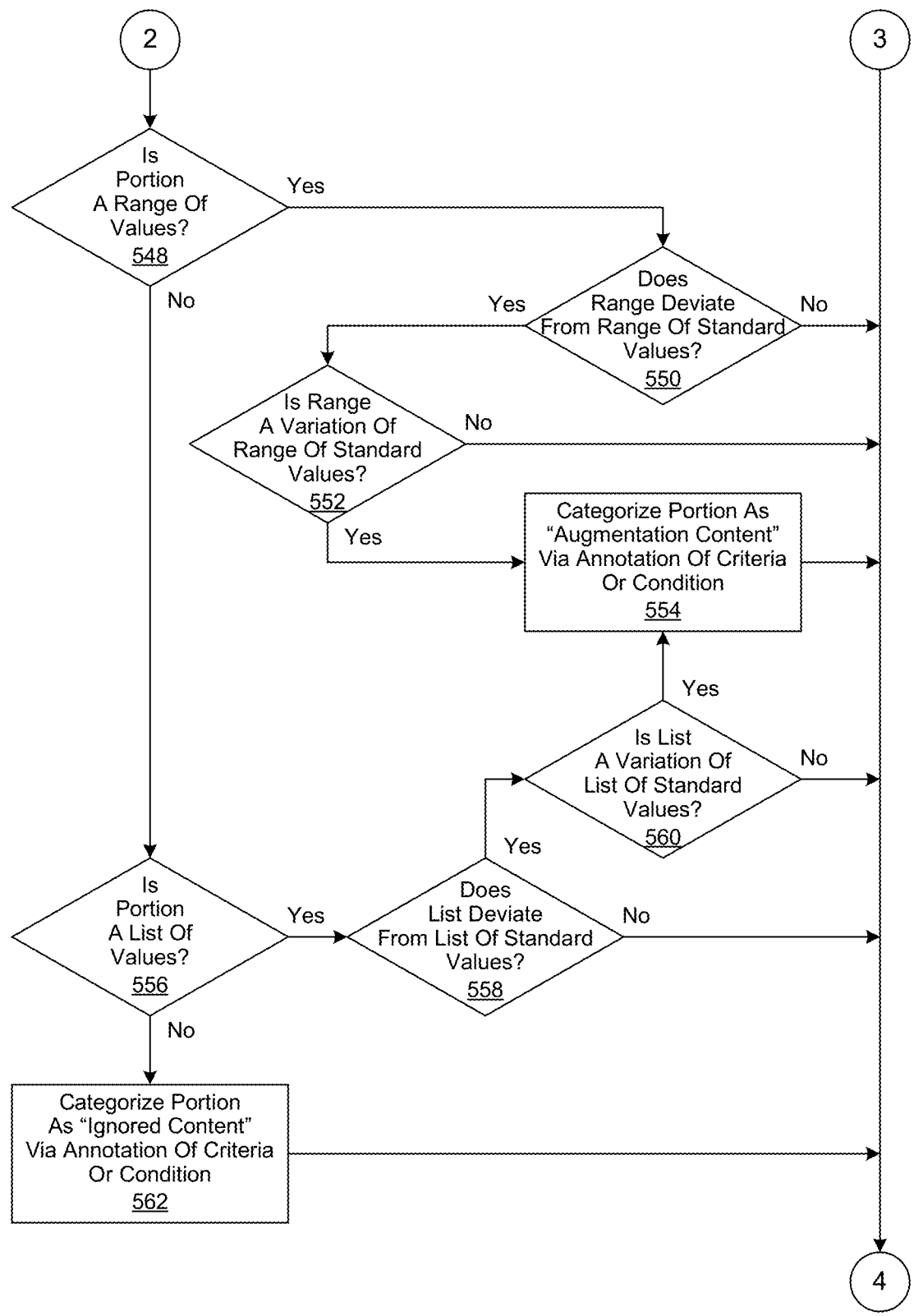
Figure 5D:
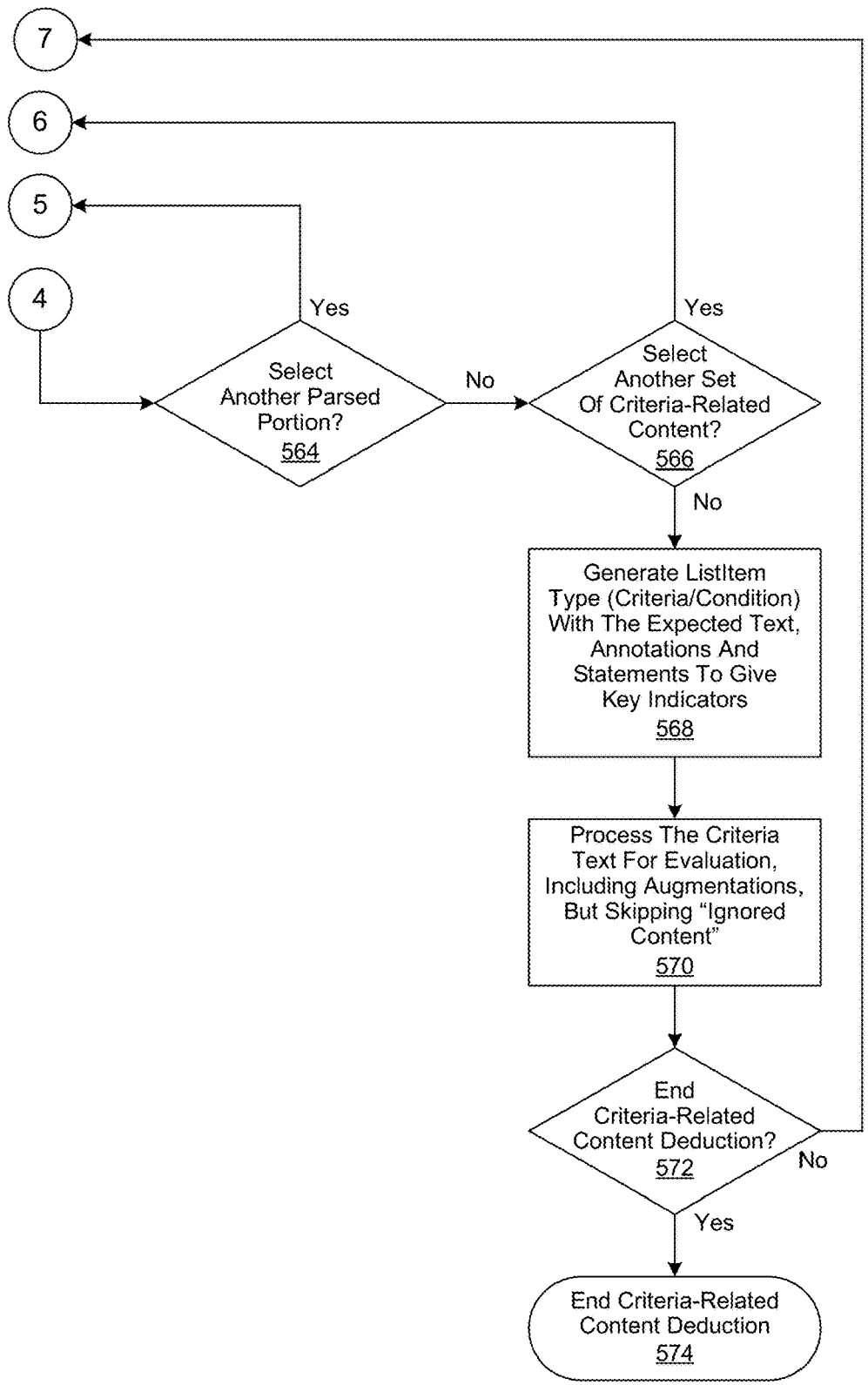

FIG. 3 is a generalized depiction of criteria-related content deductions implemented in accordance with an embodiment of the invention. In various embodiments, a criteria or condition is evaluated to exclude definitions, clarifications and restrictions such that they do not skew scoring and evaluation of the criteria. In these embodiments, deduction operations are performed to determine whether individual definitions, clarifications and restrictions should be ignored or used to augment the criteria, but not become a criterion or condition themselves. As used herein, criteria broadly refer to treatment rules or principles related to a prospective medical treatment. As an example, an individual criterion may have an associated value, such as the patient must be less than 60 years of age, or have a Body Mass Index (BMI) value that is greater than 19 and less than 25.

In various embodiments, a body of criteria text is processed to identify criteria. The criteria text is then further processed to recognize and annotate key characteristic triggers, such as parentheses, brackets, colons, line indents, or definitions following or preceding a statement that may indicate a set of content related to various criteria. In certain embodiments, the set of criteria-related content is in the proximity of an associated criterion in the criteria text.

In these and other embodiments, the set of criteria-related content may include a statement, a definition, a clarification, a restriction, a formula, a range of values, or a list. In certain embodiments, the set of criteria-related content is processed to augment the criteria or condition. In these embodiments, the set of criteria-related content does not become a separate criteria or condition for evaluation. In one embodiment, the augmentation is performed by appending the additional content to the criteria or condition. The method used to perform the augmentation or appending is a matter of design choice.

In various embodiments, the set of criteria-related content is compared to known formulae, definitions, and key attribute values from standards, the results of which are then used to determine whether the set of criteria-related content should be ignored or categorized as a condition or an argument. In certain embodiments, a definition within a set of criteria-related content is evaluated directly, instead of the original statement. As an example, a criteria may include "high-risk (intermediate-2 or high by IPSS r>10% blasts, including CMML)." In this example, the criteria-related content within the parentheses is a definition that is subsequently used to evaluate the criterion. As another example, a criteria may include "MDS (Low, INT-1 by IPSS, or hypocellular)." In this example, the criteria-related content within the parentheses is not just a definition, but additional criteria as well. Skilled practitioners of the art will recognize that many such embodiments are possible and the foregoing is not intended to limit the spirit, scope or intent of the invention.

Referring now to FIG. 3, a set of criteria text 300 contains criteria 312, 332, 342, which is parsed to find key characteristic triggers 316, 318, 336, 346, such as parentheses, brackets, colons, line indents, or definitions following or preceding a statement that may indicate a set of content related to various criteria. In various embodiments, these triggers serve as points of reference that are implemented to identify an associated set of criteria-related content 320 338, 348, which is then processed to determine whether it is annotated to be ignored 350 or used to augment 322, 334 the criteria during its evaluation.

In certain embodiments, if a phrase or sentence within the set of criteria-related content is determined to be a definition according to a Unified Medical Language System (UMLS) or a dictionary search, then it is annotated as a definition and is ignored when the criteria is evaluated. In various embodiments, if the set of criteria-related content contains attributes from UMLS, or as defined by a dictionary with equality and values assigned, it is annotated to be used to augment the normal values associated with the criteria. In certain embodiments, if the criteria-related content contains mathematical values or ranges, they are checked against a formula data set, or standard sets, to determine whether they match or are within range of expected values. If so, then the set of criteria-related content is annotated to be ignored when the criteria is evaluated. If not, then the set of criteria-related content is annotated to be used to augment the normal values or ranges associated with the criteria.

FIG. 4 shows the display of criteria and criteria-related content that has been visualized in error within a user interface (UI) window implemented in accordance with an embodiment of the invention. In this embodiment, a set of criteria text 404 is displayed within a UI window 402, along with criteria-related content that has been visualized in error 406 as a result of the invention not being implemented as described in greater detail herein.

FIGS. 5A through 5D are a generalized flowchart of the performance of criteria-related content deduction operations implemented in accordance with an embodiment of the invention. In this embodiment, criteria-related content deduction operations are begun in step 502, followed by the selection of a target criteria text in step 504. Delimiter markers (e.g., comma, semicolon, period, new line, etc.) are then used in step 506 to parse the criteria text to identify criteria, followed by the selection of a delimited portion of the parsed criteria in step 508 for further parsing operations. The selected portion of the parsed criteria is then re-parsed in step 510 to identify key characteristic triggers described in greater detail herein.

A determination is then made in step 512 whether one or more trigger points have been identified. If so, then a set of trigger points is selected in step 514 to process, followed by annotating content corresponding to the set of trigger points as a set of criteria-related content in step 516. The set of criteria-related content is then associated with its corresponding criteria in step 518 for further evaluation. A determination is then made in step 520 whether to select another set of trigger points for processing. If so, the process is continued, proceeding with step 514. Otherwise, or if it was determined in step 512 that no trigger points were identified, then a determination is made in step 522 whether to select another delimited portion of parsed criteria text to re-parse. If so, then then the process is continued, proceeding with step 508. Otherwise, a set of criteria-related content is selected in step 524 for processing.

The selected set of criteria-related content is then parsed and labeled for identification in step 526, followed by the selection of a parsed portion of the set of criteria-related content in step 528 for additional processing. The selected portion of the set of criteria-related content is then processed in step 530 to determine whether is a statement, a formula, a range, or a list of values. The method by which the selected portion of the set of criteria-related content is processed to determine whether is a statement, a formula, a range, or a list of values is a matter a design choice.

A determination is then made in step 532 whether the selected portion of the set of criteria-related content is a statement. If so, then a determination is made in step 534 whether the statement matches a known definition. If so, then a determination is made in step 536 whether the statement passes a dictionary check. If so, then the portion of the set of criteria-related content is categorized as "ignored content" via annotation of its associated criteria or condition in step 538. The method by which it is determined that the statement matches a known definition, and whether it passes the dictionary check, is a matter of design choice.

However, if it was determined in step 532 that the portion of the set of criteria-related content was not a statement, then a determination is made in step 540 whether the portion of the set of criteria-related content is a formula. If so, then a determination is made in step 542 whether the formula matches a known formula store or Unified Medical Language System (UMLS) formula. If so, then a determination is made in step 536 whether the values of the formula are different than those expected. If so, then the portion of the set of criteria-related content is categorized as "augmentation content" via annotation of its associated criteria or condition in step 546. The method by which it is determined that the formula matches a known formula, and whether the values of the formula are different than those expected, is a matter of design choice.

However, if it was determined in step 540 that the portion of the set of criteria-related content was not a formula, then a determination is made in step 548 whether the portion of the set of criteria-related content is a range of values. If so, then a determination is made in step 550 whether the range of values deviates from a known range of standard values. If so, then a determination is made in step 552 whether the range of values is a variation of a known range of standard values. If so, then the portion of the set of criteria-related content is categorized as "augmentation content" via annotation of its associated criteria or condition in step 554. The method by which it is determined that the range of values deviates from a known range of standard values, and whether the range of values is a variation of a known range of standard values, is a matter of design choice.

However, if it was determined in step 548 that the portion of the set of criteria-related content was not a range of values, then a determination is made in step 556 whether the portion of the set of criteria-related content is a list of values. If so, then a determination is made in step 558 whether the list of values deviates from a known list of standard values. If so, then a determination is made in step 560 whether the range of values is a variation of a known list of standard values. If so, then the portion of the set of criteria-related content is categorized as "augmentation content" via annotation of its associated criteria or condition in step 554. The method by which it is determined that the list of values deviates from a known range of standard values, and whether the list of values is a variation of a known range of standard values, is a matter of design choice.

However, if it was determined in step 556 that the portion of the set of criteria-related content is a not a list of values, then the portion of the set of criteria-related content is categorized as "ignored content" via annotation of its associated criteria or condition in step 562. Thereafter, or if the determinations made in steps 534, 536, 542, 544, 550, 552, 558 or 560, or the operations are completed in steps 538, 546, or 554, a determination is made in step 564 whether to select another parsed portion of the set of criteria-related content for processing. If so, then the process is continued, proceeding with step 528. If not, then a determination is made in step 566 whether to select another set of criteria-related content for processing. If so, then the process is continued, proceeding with step 524.

However, if it is determined in step 566 not to select another set of criteria-related content for processing, then the expected text, annotations and statements are processed in step 568 to generate a List Item type to give key indicators. The criteria text, including sets of criteria-related content categorized as "augmentation content," but excluding sets of criteria-related content categorized as "ignored content," is then processed for evaluation in step 570. A determination is then made in step 572 whether to end criteria-related content deduction operations. If not, then the process is continued, proceeding with step 504. Otherwise, criteria-related content deduction operations are ended in step 574.

Although the present invention has been described in detail, it should be understood that various changes, substitutions and alterations can be made hereto without departing from the spirit and scope of the invention as defined by the appended claims.

What is claimed is:

1. A computer-implemented method for analyzing and deducing criteria-related content for evaluation via a criteria deduction system executing on a hardware processor, the criteria deduction system being associated with a question/answer (QA) system capable of answering questions, comprising:
    receiving an input corpus to the criteria deduction system via a network, the input corpus comprising a plurality of guidelines, each of the plurality of guidelines comprising criteria, the criteria comprising principles related to each of the plurality of guidelines and the criteria comprises a treatment rule related to a prospective medical treatment;
    processing criteria text from the plurality of guidelines to identify the criteria, the processing performed by the QA system capable of answering questions;
    analyzing, via the criteria deduction system, the criteria text to identify a set of criteria-related content associated with the criteria, the criteria-related content comprising content that skews scoring and evaluation of the criteria when the QA system is answering a question using the criteria;
    processing, via the criteria deduction system, the set of criteria-related content to determine a relationship of the criteria to an associated guideline;
    annotating, via the criteria deduction system, the set of criteria-related content according to the determined relationship, wherein the annotation compromises ignored content to identify content to be excluded from an evaluation of the prospective medical treatment; and augmentation content to adjust the evaluation of the prospective medical treatment; and
    using the set of criteria-related content in accordance with its annotation when processing the criteria for the evaluation; and wherein,
    the set of criteria-related content is in proximity of an associated criterion in the criteria text; and,
    the set of criteria-related content is identified by a trigger associated with the criteria, the trigger comprising a key characteristic trigger, the key characteristic trigger serving as a point of reference without user intervention to identify an associated set of criteria-related content.

2. The method of claim 1, wherein the key characteristic trigger is a member of the set of:
    a set of parentheses;
    a set of brackets;
    a colon;
    a line indent; and
    a definition.

3. The method of claim 1, wherein the relationship is a member of the set of:
    a statement;
    a definition;
    a clarification;
    a restriction;
    a formula;
    a range of values; and
    a list.

4. The method of claim 1, wherein the
    augmentation content comprising content that is treated as an augmentation to the criteria during criteria processing; and
    the ignored content ignored content comprising content that can be ignored during criteria processing.

5. The method of claim 4, wherein the processing the criteria for evaluation comprises:
    excluding content from an evaluation annotated to be ignored; and
    adjusting evaluation of the criteria based on augmentation content.

* * * * *